United States Patent [19]

Bartlett

[11] Patent Number: 4,947,896
[45] Date of Patent: Aug. 14, 1990

[54] LARYNGOSCOPE

[76] Inventor: Robert L. Bartlett, 149 Rudder Ct., Lexington, S.C. 29072

[21] Appl. No.: 267,131

[22] Filed: Nov. 4, 1988

[51] Int. Cl.⁵ .............................................. A61B 1/26
[52] U.S. Cl. ........................................ 128/11; 128/10
[58] Field of Search ..................... 128/10, 11, 12, 13, 128/15, 16, 207.14, 207.15, 304; 433/140

[56] References Cited

U.S. PATENT DOCUMENTS

| | | | |
|---|---|---|---|
| 1,613,373 | 1/1927 | Beck | 128/15 |
| 2,433,705 | 12/1947 | Palmeter | 128/10 |
| 2,648,329 | 8/1953 | Morch | 128/11 |
| 2,708,437 | 5/1955 | Hutchins | 128/7 |
| 3,638,644 | 2/1972 | Reick | 128/16 |
| 3,771,514 | 11/1973 | Huffman et al. | 128/11 |
| 3,826,248 | 7/1974 | Gobels | 128/11 |
| 4,126,127 | 11/1978 | May | 128/11 |
| 4,408,598 | 10/1983 | Ueda | 128/4 |
| 4,425,909 | 1/1984 | Rieser | 128/16 |
| 4,432,350 | 2/1984 | Breslau et al. | 128/10 |
| 4,527,553 | 7/1985 | Upsher | 128/16 |
| 4,832,020 | 5/1989 | Augustine | 128/10 |
| 4,834,077 | 5/1989 | Sun | 128/16 |

*Primary Examiner*—William H. Grieb
*Assistant Examiner*—Mark S. Graham
*Attorney, Agent, or Firm*—Dority & Manning

[57] ABSTRACT

A laryngoscope has a blade and a removably attached handle, which can be fixed to the blade at a desired angle. The blade has a predetermined cross-section of compound curvature defining a plurality of channels, including a viewing channel and a plurality of service channels. The blade also supports twin halogen lights which project light down opposing axial sides of the blade structure. Electric wires run in the service channels between the lights and batteries received in the handle. An adjustable position suction tube is entrained in the blade in another service channel, with an adjustment actuator supported on the handle. A roughened surface is formed in a tongue contact area of the blade to enhance frictional engagement of the patient's tongue.

24 Claims, 4 Drawing Sheets

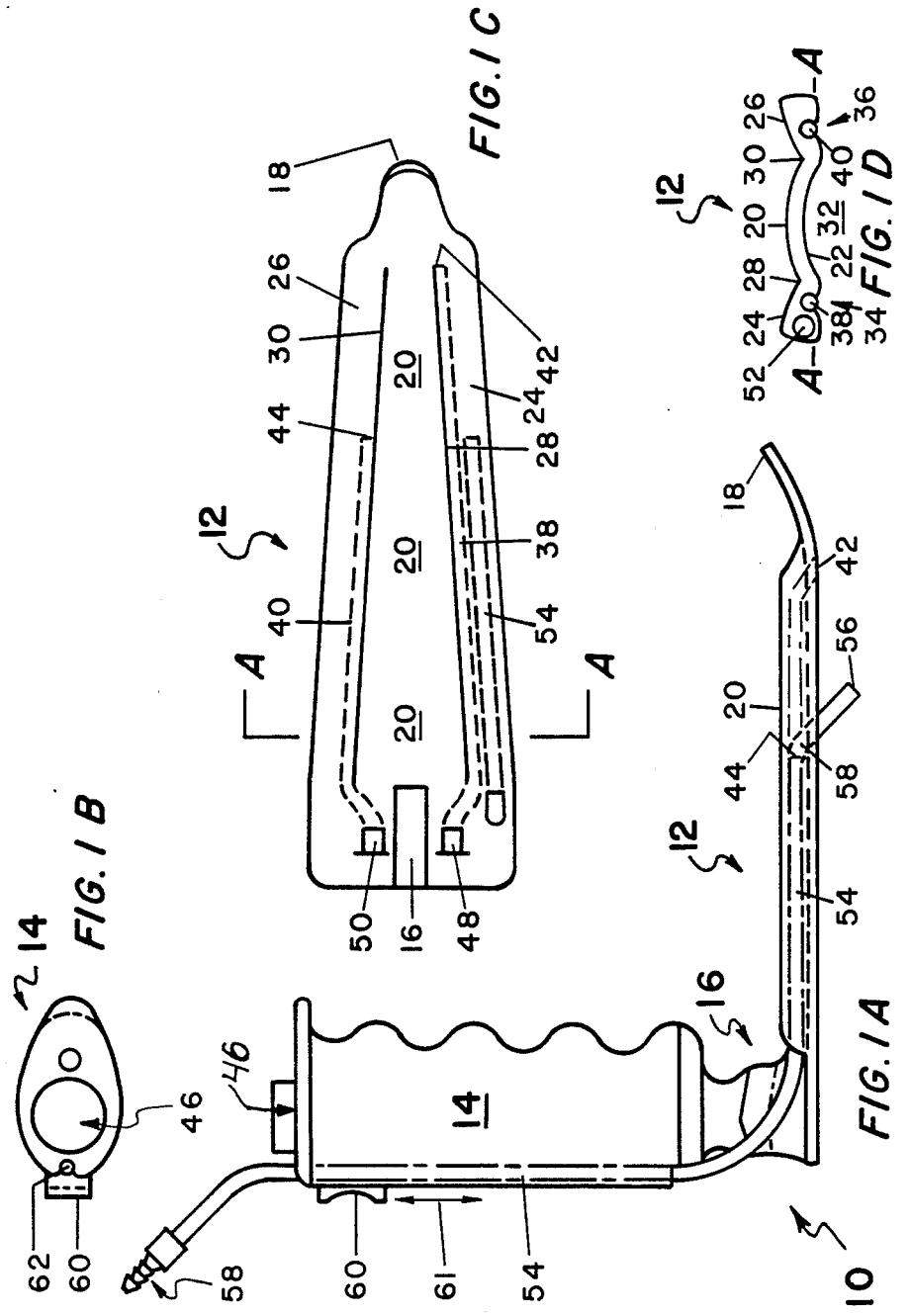

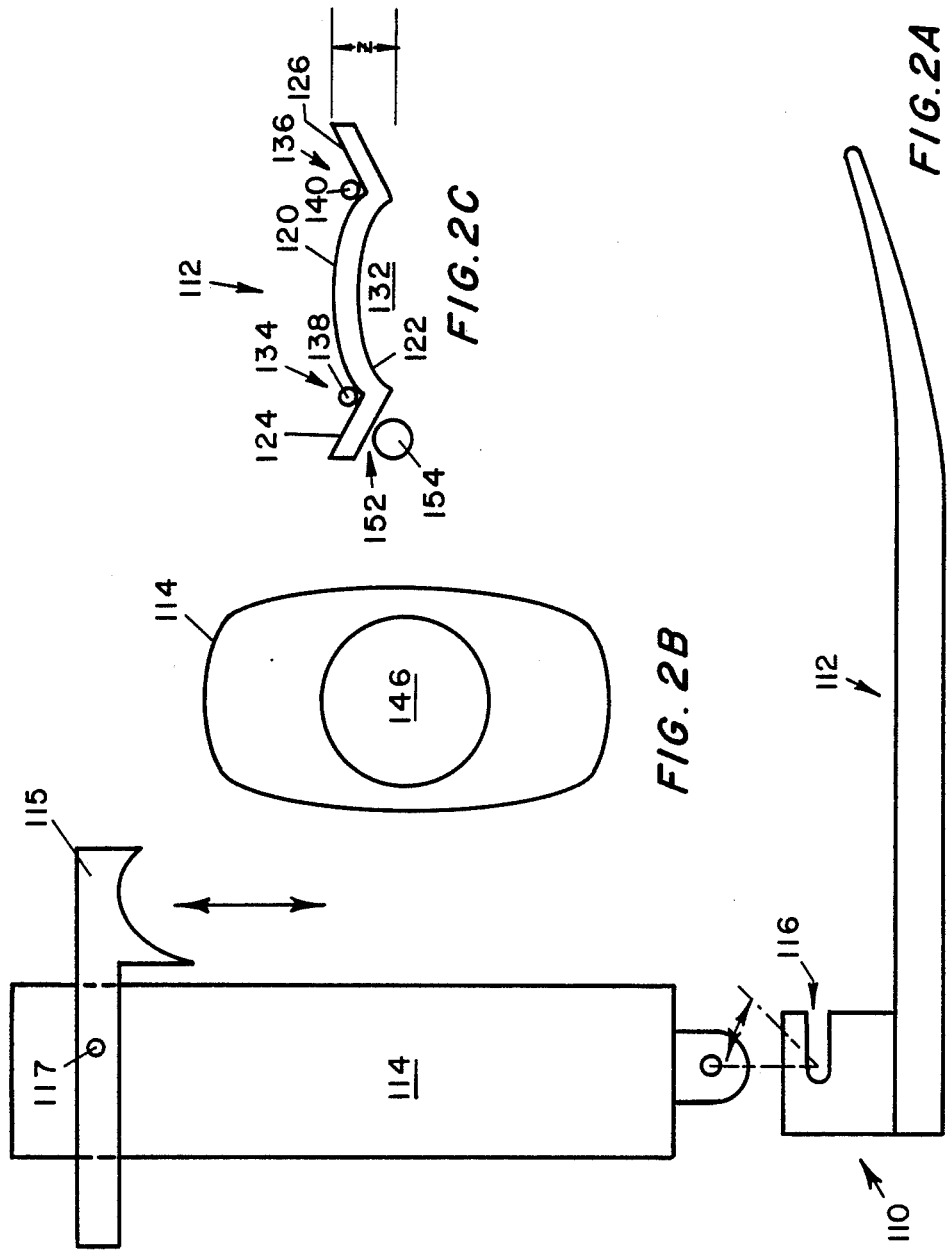

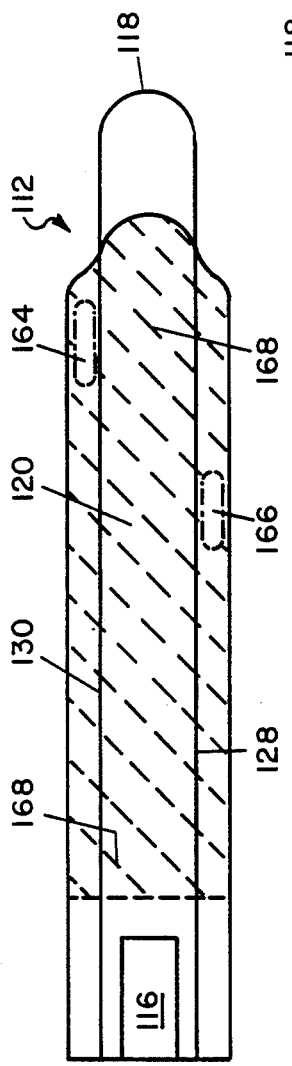
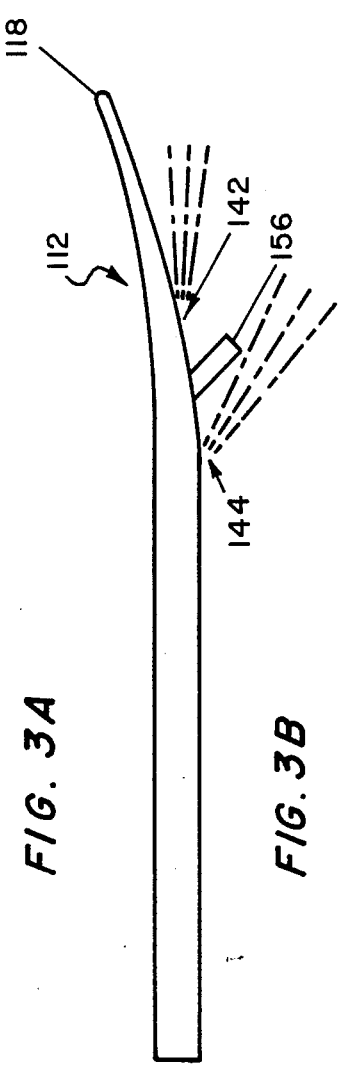
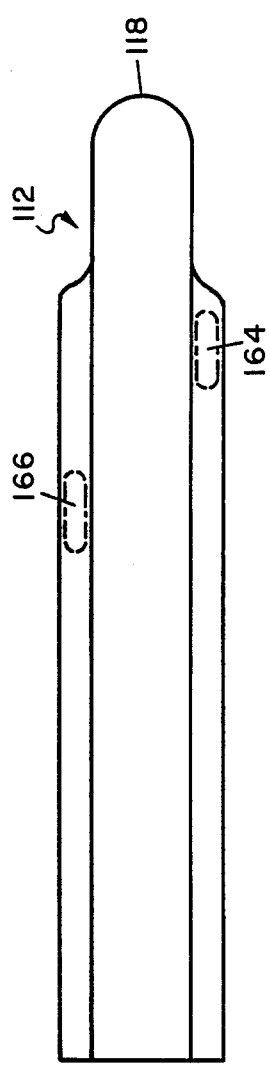
FIG. 3A
FIG. 3B
FIG. 3C

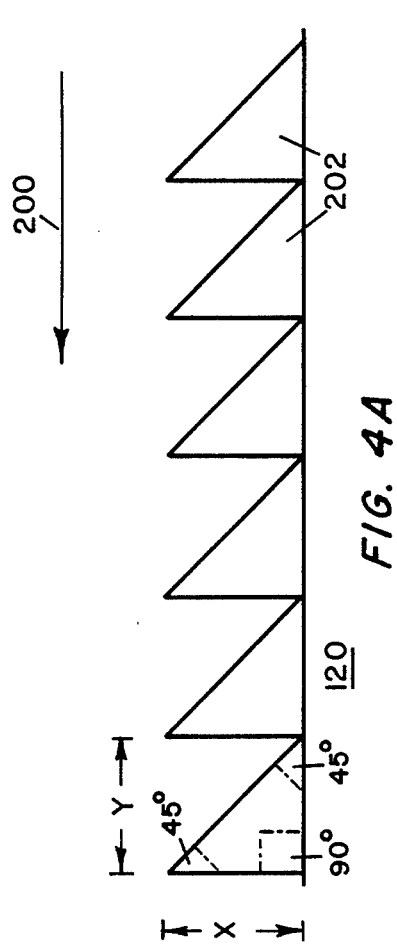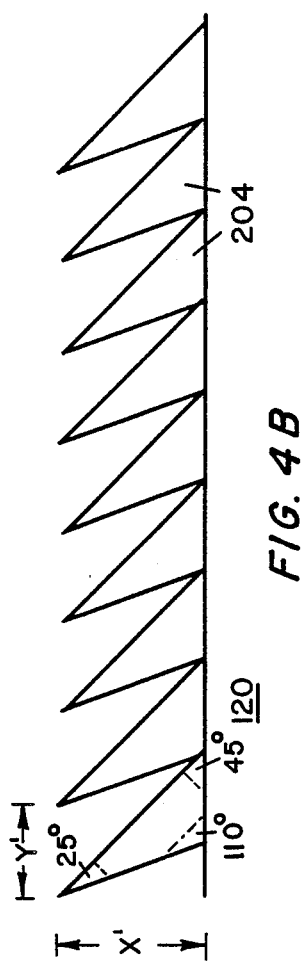

LARYNGOSCOPE

BACKGROUND OF THE INVENTION

This invention concerns a medical instrument in general, and in particular a laryngoscope having improved illumination and tongue retention features.

In the course of providing patient care, particularly of an emergency nature, it is frequently necessary or desirable to examine and/or clear the mouth and throat of the patient. In general, instruments known as laryngoscopes are widely known and used for this purpose.

A typical laryngoscope includes a blade member for insertion into the mouth and throat of a patient, and a handle attached to the blade for manipulation of the blade by a doctor, nurse, or emergency medical personnel. Typically, the patient is placed on his or her back, and the patient's chin is lifted so as to place the patient in the so-called sniffer position. As the head and neck of the patient are properly situated to achieve such position, the patient's tongue generally falls downward towards the roof of the patient's mouth. Thus, one of the functions of prior art laryngoscopes is to engage and hold the patient's tongue to permit viewing of the throat and tracheal process of the patient. Also, the instrument is useful in physically positioning the patient for full entry of the laryngoscope blade, all of which is often a prerequisite to intubation of the patient. The general concepts regarding introduction and use of laryngoscopes is known in the art, as represented for example by Rieser, U.S. Pat. No. 4,425,909, the disclosure of which as relates to such concepts is incorporated herein by reference.

The intubation procedure mentioned above, i.e. introducing a tube or the like into the trachea, requires an unobstructed view. Often, the patient's mouth and throat may contain fluid and/or solid materials which must be removed to permit intubation, or other desired procedures. Additionally, although it is generally known to provide some form of illumination in conjunction with the laryngoscope blade, temporary obstruction of such lighting due to fluids or other materials, can cause considerable problems, especially if the lighting blockage occurs at the critical moments of actual intubation.

As mentioned above, the laryngoscope blade typically engages and restricts subsequent movement of the patient's tongue as the blade is introduced into the mouth and throat of the patient. However, particularly whenever liquids in the patient's mouth keep the tongue moistened or wet, a relatively slippery condition of the tongue can make its engagement difficult with a smooth metal blade.

SUMMARY OF THE INVENTION

The present invention recognizes and addresses the foregoing disadvantages, and others, of prior art laryngoscopes. Accordingly, it is one general object of the present invention to provide an improved laryngoscope. Another object is provision of a laryngoscope which permits improved tracheal viewing conditions, generally.

It is a more particular object to provide a laryngoscope having improved tongue engagement features. It is another more particular object to provide a laryngoscope with improved illumination features.

Another present object is to provide an examination instrument, such as a laryngoscope, which incorporates adjustable suctioning, to permit adjustments to the position of a suction tube after entry of the instrument into a patient's mouth and throat, but without the necessity of moving the instrument itself.

Alternatively, it is an object to provide for adjustment of an inserted tube which through positive air pressure introduces rather than withdraws materials from a patient's mouth or throat. In particular, it is an object to permit the introduction of oxygen or the like.

A more particular object of the present invention is to provide a gull wing type blade for a laryngoscope, which through a compound curvature thereof establishes a plurality of channels or passageways, including at least one passageway for unobstructed viewing, and at least one service passageway for receiving tubes, electric wire conduits, or the like.

Regarding improved frictional tongue engagement, it is a more particular present object to provide a laryngoscope with a textured or roughened tongue contact surface, which is especially helpful in engaging and securing a patient's tongue whenever such tongue is wet. It is an even more particular object to provide for texturing on a tongue contact surface which is at least slightly biased to have a relatively lower insertion frictional coefficient, but a relatively higher withdrawal frictional coefficient.

It is another present object to provide an improved illuminating laryngoscope, which is battery operated, and which has an adjustable handle angle.

In addition to the foregoing, it is another general object to provide a laryngoscope having a twin light system, with partial redundancy, for minimizing the likelihood of lighting obstruction, especially during critical moments.

It is another general object to provide a laryngoscope construction which may be practiced in different scaled sizes, to permit use thereof with all manner of patients, such as including children and adults.

Those of ordinary skill in the art will understand and appreciate that various modifications and variations to the specific exemplary constructions discussed herein may be practiced without departing from the spirit and scope of the present invention. Moreover, all such variations and the like are intended to come within the spirit and scope of this invention by virtue of present reference thereto.

In addition, it will be understood that various combinations of presently disclosed features may be practiced as an exemplary embodiments in accordance with this invention. One exemplary present construction relates to a laryngoscope having blade means for being inserted into the mouth of a patient, such blade means having a primary contact surface for engagement with the tongue of such patient; and handle means attached to the blade means for permitting manipulation of the blade means including controlled introduction thereof into the mouth of a patient with the primary contact surface oriented for engagement with the tongue of such patient. In such a construction, the primary contact surface is preferably roughened for enhanced frictional engagement of the primary contact surface with the patient's tongue, whereby such tongue may be relatively secured upon introduction of the blade means into the patient's mouth for improved unobstructed viewing of the patient's tracheal process.

In another exemplary present construction, the foregoing exemplary blade means comprises a generally elongated member having a predetermined cross-section of compound curvature, such cross-section including a convex surface defining a primary tongue contact surface, and further including a concave surface on an opposite side of the blade means from the convex surface, such concave surface defining along the blade means a viewing channel for unobstructed viewing of the patient's tracheal process. During such viewing, the patient's tongue is situated on the other side of the blade means from the viewing channel.

Still another exemplary embodiment in accordance with this invention is directed to the combination of a handle for controlled manipulation of the laryngoscope; and an insertable, elongated blade attached to the handle for being placed in the mouth of a patient. The blade has a cross-section of compound curvature for defining along the blade a plurality of channels into a patient's mouth, including an unobstructed viewing channel for observation of the patient's tracheal process, and at least one service channel for receiving a tube, wire conduit or the like. With such a construction, the blade preferably further includes at least one relatively coarser surface on one side thereof for enhanced engagement with the patient's tongue whenever the blade is situated in a patient's mouth through manipulation thereof by a user with the handle.

Still another present construction includes a laryngoscope comprising an elongated blade member for insertion into a patient's mouth, such blade member having a compound curvature establishing a plurality of channels in relation to the patient's mouth and throat when inserted therein. Such channels include an unobstructed viewing channel and three separate service channels. The laryngoscope further includes a handle attached to the blade and having electric batteries therein. The blade member has a coarsened surface thereon, which defines a tongue contact surface. A pair of separate light means are supported on the blade member. A pair of separate electric wire means are interconnected between the batteries and the light means, and situated in two of the service channels established by the blade member compound curvature. Also, a tubular member is received in the remaining service channel. One end of the tubular member terminates relatively adjacent the blade member, while the other end extends outward therefrom. Thus, positive or negative pressure applied to the tubular member other end permits controlled introduction or removal, respectively, through the tubular member, of materials relative to the patient's mouth and throat.

Other objects, features, and aspects of the present invention are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which:

FIGS. 1A, 1B, 1C and 1D illustrate various views of a first embodiment in accordance with the present invention;

FIGS. 2A, 2B, and 2C illustrate particular views of a second exemplary embodiment in accordance with the present invention;

FIGS. 3A, 3B, and 3C illustrate top, side, and bottom elevational views, respectively, of the blade component of the second embodiment illustrated in present FIGS. 2A and 2C; and FIGS. 4A, and 4B illustrate two exemplary roughened surfaces, in greatly enlarged detail, for alternative use in conjunction with tongue contact surfaces of a blade in accordance with one aspect of the present invention.

Repeat use of reference characters in the present specification and drawings is intended to represent same or analogous features or elements of the invention.

DETAILED DESCRIPTION OF THE PREFERRED EMBODIMENTS

It is to be understood by those of ordinary skill in the art that the present discussion is a description of exemplary embodiments only, and is not intended as limiting the broader aspects of the present invention, which broader aspects are embodied in the exemplary constructions. Referring to the first such embodiment as represented in present FIGS. 1A through 1D, laryngoscope 10 comprises a combination of two basic elements, blade means 12 and handle means 14. The two members 12 and 14 may be fixed and permanently attached to one another, or removably attached at a coupling 16. Such coupling may be of any convenient nature, but preferably includes a ratchet or wing nut type mechanism to permit relative pivotal movement between members 12 and 14, which may be secured once a desired relative position is established. Most preferably, the angle between the blade means and the handle means may be selectively established, generally in a range of from about 45° to about 90°.

FIG. 1A illustrates a side view of laryngoscope 10 (with members 12 and 14 attached), while FIG. 1B illustrates a top view of handle means 14 only, and FIG. 1C illustrates a top view of blade means 12 only. FIG. 1D is a cross-sectional view of blade means 12, taken along the line A—A, as illustrated in FIG. 1C. FIG. 1D illustrates one preferred exemplary predetermined cross-section of such blade means, which generally has a compound curvature in accordance with this invention. For present purposes, the term compound curvature is intended to mean that the cross-section has multiple areas of different curvature, rather than a single form of curvature, such as a circle, oval, ellipse, or the like.

The first embodiment is described hereinafter with collective reference to FIGS. 1A through 1D, in which figures dotted line illustrations are intended as representing features which appear below or behind the hard surface features otherwise illustrated in the indicated views (i.e., the dotted line features are normally hidden behind the solid line features). Blade means 12, particularly as represented in FIG. 1C, has a generally tapered width which terminates in a rounded distal tip 18. Tip 18 is turned upward (see FIG. 1A), preferably for improved engagement of a patient's tongue against a convex primary tongue contact surface 20. For the sake of clarity, surface 20 in FIG. 1C is not hatched or otherwise represented as having any particular surface characteristics. However, according to one alternative feature of the present invention, such primary tongue contact surface preferably is treated so as to become relatively roughened, i.e. provided a coarse surface, for improved frictional engagement with a patient's tongue. Embodiments of this invention are not strictly limited to inclusion of such a feature. However, specific exemplary roughened surface features are discussed below in connection with FIG. 4A and 4B.

Convex surface 20 is on an opposite side of blade means 12 from a corresponding concave surface 22 thereof. Laterally from each side edge of convex surface 20 are provided flanges, i.e., gull wing members 24 and 26. Junctures 28 and 30 are respectively formed between gull wing members 24 and 26, and convex surface 20.

As perhaps best represented in FIG. 1D, a viewing channel or passageway 32 is defined or formed by the concave surface 22. Similarly, the compound curvature of the remaining cross-sectional structure (in this instance, particularly gull wing members 24 and 26) defines service channels or passageways 34 and 36. Preferably such channels receive electric wire conduits or the like 38 and 40 for transferring electric power to a pair of lights 42 and 44, respectively, associated therewith. A variety of lamps, such as halogen lights, or the like, may be used. While inclusion of a light bulb in a laryngoscope-type instrument is generally known, the present construction provides certain advantages. For example, the compound curvature cross-sectional structure of present FIG. 1D unobtrusively accommodates service channels 34 and 36, which results in provision of two separate lights along opposing axial sides of blade means 12. Further in accordance with the present invention, lamp 42 is situated in a relative distal position, while lamp 44 is more proximal to handle means 14. Thus, both axial and lateral separation of the lamps enhances lighting with the laryngoscope by minimizing the likelihood that such lighting will become obstructed by the unexpected introduction of material, at least in a short term, critical time frame.

While various arrangements may be practiced, preferably handle means 14 receives and supports therein appropriate electric batteries 46 or the like for powering lamps 42 and 44 through respective contacts 48 and 50. In this instance, member 46 is preferably a screw-mounted or otherwise secured cap for holding batteries inside the handle means, where proper electrical contacts and wiring of generally well-known type (not shown) are provided. Contacts 48 and 50 are brought into electrical interconnection with corresponding contacts from handle means 14 in the area of coupling 16, whenever such two members 12 and 14 are attached. Thus, while a separate on/off switch may be provided, no switch is necessary since the lamps are automatically illuminated responsive to a fully assembled condition of the laryngoscope (when batteries are inserted).

Either one or both of gull wing members 24 and 26 may be further utilized for forming another (a third) service passageway, such as passageway 52. In this instance, such passageway preferably receives a tubular member 54 which may be alternately used as a suction tube for removing materials from a patient's mouth and throat, or as a tube for inserting oxygen or other materials into the patient's mouth and throat. It may be particularly desirable to introduce oxygen during certain procedures with certain classes of patients, such as during intubation of small children.

Present FIGS. 1A and 1B in particular illustrate a further optional feature of this invention, wherein tubular member 54 is adjustable so that a free end 56 thereof (preferably directed away from blade means 12) may be axially positioned along such blade means without having to reposition either the blade means or the handle means. In this instance, blade means 12 is representatively illustrated with a shoulder element 58 for deflecting end 56 of tube 54 away from blade means 12, which relative spacing improves suctioning operations with tube 54. With tubular member 54 entrained along blade means 12, preferably in a service channel such as passageway 52 thereof, the other end 58 of such tubular member is situated away from blade means 12. While various constructions may be practiced, a sliding member 60, movable in the direction of double-headed arrow 61, and attached or otherwise connected or associated with tubular member 54, may be entrained in a channel 62 or the like formed by handle means 14, whereby the position of end 56 may be controlled by a user through manipulation of member 60. Thus, adjustable suction (or adjustable introduction of materials) is provided without requiring repositioning or movement of blade means 12 or handle means 14, once the laryngoscope is desirably seated in a patient's mouth and throat.

Based upon the foregoing description, particularly with reference to FIGS. 1A through 1D, it is believed that one of ordinary skill in the art will appreciate that convex surface 20 is intended to be on a "tongue" side of blade means 12, while concave surface 22 is on a "trachea" or viewing side of blade means 12. Illumination is preferably provided on such viewing side, for best results. Furthermore, actual introduction of the instrument into a patient's mouth and throat, and a detailed description of such operation, is not specifically called for in view of general knowledge of those of ordinary skill in the art, as well as the incorporation by reference of such related disclosure from Rieser, U.S. Pat. No. 4,425,909, referenced above.

A second exemplary embodiment is discussed below, particularly with reference to FIGS. 2A through 2C. Features generally analogous to those of the first embodiment will be referenced with like 100 series numbers. For example, a laryngoscope 110 in accordance with the second exemplary embodiment has blade means 112 and handle means 114 which may be pivotally joined at connector or coupling 116.

For clarity, no tubular members or the like are illustrated in the side elevational view of FIG. 2A, though such features could be used with the second embodiment, and would incorporate preferably some form of channel or other means for guiding the tubular member along handle means 114. Instead, an exemplary adjustable grip means 115 is illustrated. By means of a set screw 117 or the like, the adjustable grip means 115 may be received about the body of handle means 114, which handle means has an outline such as represented by the cross-sectional view thereof in present FIG. 2B. Batteries 146 are again preferably supported directly in the handle means themselves. Also, as represented by the side elevational view of FIG. 2A and the cross-section of FIG. 2B, handle means 114 may be provided with a relatively straight surface, if desired, rather than the pistol grip-type construction of handle means 14 of the first embodiment.

Other differences between the first and second embodiments are apparent upon viewing the side elevational view of blade means 112 in FIG. 2A (compared with blade means 12 of FIG. 1A). FIG. 2C represents a cross-section of blade means 112, taken generally in the same relative position as the cross-sectional view of FIG. 1D with reference to blade means 12 of the first embodiment. As is apparent from such FIG. 2C, again the blade means has a predetermined cross-section of a compound curvature, preferably including a convex surface 120 and corresponding concave surface 122. While viewing passageway 132 is formed in substantially the same relationship to concave surface 122 as in the first embodiment, the other, i.e. service passageways are formed differently. In particular, gull wing areas 124 and 126 are used in conjunction with convex surface 120 for defining service passageways 134 and 136 generally on the "tongue" side of blade means 112, rather than generally on the "trachea" side of such blade means as in the first embodiment. As illustrated, respective wire conduits or the like 138 and 140 are again received in such service channels.

Though no enclosed channel is formed, a third service channel for a tubular member 154 is generally formed on the "trachea" side of blade means 112. Such third service passageway 152 is generally formed beneath gull wing member 124. A similar passageway could be utilized in the area beneath gull wing member 126. As represented by the zone Z to the right of FIG. 2C, blade means 112 makes use of its cross-sectional compound curvature to define the service passageways and the viewing passageway by virtue of the zone which is cleared by insertion of the blade means, even though no totally encircled area is provided by the configuration of the present second embodiment.

Present FIGS. 3A through 3C illustrate additional aspects of blade means 112 of the second embodiment, particularly with comparison to the blade means of the first embodiment. FIGS. 3A through 3C represent top, side, and bottom elevational views of such blade means 112, with substantially all of the associated features thereof removed for clarity in the respective illustrations. Distal tip 118 is preferably rounded, and raised as in the first embodiment. However, the width of blade means 112 is generally constant along the length thereof, until approaching distal end 118. Such feature is an alternative to the tapered width represented in the first embodiment.

Since electric wires are utilized on the tongue side of blade means 112 and since it is desired to illuminate the opposite, viewing side thereof, openings 164 and 166 may be used for projection of light therethrough, or for actual passage of the electric wires therethrough to lights mounted on the viewing side. The relative position of such openings 164 and 166 appears reversed between FIGS. 3A and 3C since they represent reverse views of blade means 112.

Side elevational view FIG. 3B illustrates preferred light projection patterns for lights 142 and 144. Since light 142 is in a relatively distal position (as discussed above), it is unblocked from an axially forward projection of light. Thus, such light becomes in a sense the primary illumination, projecting most deeply into the throat of the patient. Relatively speaking, the projection pattern from light 144 is for general illumination and background, and thus is preferably projected along a given pathway somewhat deflected from that of the illumination pattern of light 142. With such multiple facets for variety and redundancy in the illumination, the likelihood is reduced that a temporary obstruction will completely defeat illumination at a given moment.

Though not illustrated in detail, the free end 156 of the tubular member illustrated in dotted line in FIG. 3B is intended to represent that the tubular member features discussed above in conjunction with the first embodiment (including the adjustability thereof) may be completely and fully practiced with this second embodiment, if desired by the user.

With regard to the optional use of a roughened surface over the primary tongue contact area of blade means 112, the dotted line coverage 168 of FIG. 3A is intended to represented one exemplary area of such textured coverage. Examples of such textured coverage are discussed in greater detail below, with reference to FIGS. 4A and 4B. The non-dotted line marked areas of FIGS. 3A and 3C are intended to represent smooth (i.e. non-textured) surfaces.

Textured surfaces in accordance with this invention may include a wide variety of treatments to the desired surface area of the blade so as to provide enhanced frictional engagement with a patient's tongue. It is well known that the surface of a tongue is itself somewhat roughened, but it is equally well known that a wet tongue can be very slippery on a smooth metal surface. In this instance, texturing such as stippling, or other treatments of the desired surface area to enhance its frictional characteristics, will cooperate with the roughness of the tongue surface to help engage and secure same whenever the blade is applied against the tongue during normal use of the laryngoscope.

FIGS. 4A and 4B illustrate very particular exemplary embodiments of surface treatments which may be used in selected areas to impart texturing which provides a slight biasing effect in the following sense. Engagement by a tongue with either surface as represented in FIG. 4A or 4B in the direction of arrow 200 will have a relatively low (insertional) frictional coefficient. However, movement in the opposite direction (presumably a withdrawal direction) will have a relatively higher frictional coefficient as the peaks of the illustrated structures 202 (FIG. 4A) and 204 (FIG. 4B) are encountered.

While considerable variety may be practiced in the relative height and width of such repeating members, the X and Y dimensions of members 202 of FIG. 4A are approximately 0.015 inches each. As illustrated, a right triangle is formed so that the base angle is 90° relative surface 120, while the other angles are approximately 45° each.

The biasing effect of the exemplary embodiment of present FIG. 4B is slightly higher in that the tips of repeating elements 204 are relatively sharper and more steeply angled against movement in a direction opposite to arrow 200. In this second exemplary embodiment of a specific roughened surface construction, height X' is again 0.015 inches while the width dimension Y' is reduced to 0.01 inches. The right angle is replaced with a larger angle of about 110°. One of the other angles is correspondingly decreased to 25°, while the second remains at 45°. Various constructions may be practiced for providing desired frictional engagement characteristics, even including mixtures of different constructions or surface features in a single relatively roughened surface area, or with different constructions in different specific areas.

In addition to the foregoing exemplary details of dimensional characteristics for given exemplary embodiments, the following exemplary details are provided in connection with other present features. For example, though none of the present drawings are intended as being drawn to scale, the overall blade length in FIG. 3A for an adult size laryngoscope is approximately seven inches. The width of the blade is approximately 1.18 inches, with approximately ¼" between the side edge of the blade and the junction between such lateral gull wing member and the convex surface 120. With reference to FIG. 3B, the relative zone thickness of the blade from the bottom of the tracheal side thereof to the top of the distal tip tongue side is approximately ¾".

Also, with respect to electrical connections and the like, numerous variations may be practiced, but two "C" batteries providing a nominal three volts is adequate to power suitable lights. Such batteries may be lithium, nickel cadium, or other constructions, while such lights are preferably halogen or the like.

All of the foregoing dimensions, and corresponding constructions, may be variously sized in relative proportion for use with different patients, such as children versus adults.

While specific exemplary embodiments have been discussed in detail, it is to be understood that the present invention is not limited to such. For example, while two lights have been discussed, each light may instead represent a light position, whereat a multiplicity such as two or more actual light bulbs are used, each being directed on slightly different paths. Likewise, combinations of presently disclosed features not specifically illustrated in a single embodiment may be practiced. For example, a pistol-type grip (FIG. 1A) may be used with a relatively straight blade means (FIG. 3A) with either one, or an alternative, surface configuration from FIGS. 4A or 4B. All such variations are intended to come within the spirit and scope of the present invention, which is further set forth in the appended claims.

What is claimed is:

1. A laryngoscope for use with a patient to obtain improved unobstructed viewing of the patient's tracheal process, said laryngoscope comprising:
    blade means for being inserted into the mouth of a patient, said blade means having a tip, a cross-section with a compound curvature, including at least one convex surface on one side of said blade means, lateral gull wing members angled back towards said convex side, and a corresponding concave surface on an opposite side of said blade means, said concave surface forming a viewing passageway into a patient's throat, with the patient's tongue received on said side having said at least one convex surface; and
    handle means, attached to said blade means for permitting manipulation of said blade means including controlled introduction thereof into the mouth of a patient with said side having said at least one convex surface oriented for engagement with the tongue of such patient;
    wherein said side having said at least one convex surface is relatively roughened for enhanced frictional engagement thereof with the patient's mount for improved unobstructed viewing of the patient's tracheal process.

2. A laryngoscope as in claim 1, wherein:
    said lateral gull wing members comprise a pair of flanges respectively projecting laterally from opposing side edges of said convex surface, with the respective junctures between said convex surface and such flanges defining a pair of service passageways; and
    said laryngoscope further includes a pair of lights supported on said blade means, batteries carried on said handle means, and respective wire pairs interconnecting said batteries with said lights to power same for illuminating a patient's mouth and throat;
    wherein said respective wire pairs pass respectively through said pair of service passageways.

3. A laryngoscope as in claim 2, wherein one of said lights is situated relatively near the tip of said blade means, and the other of said lights is situated a predetermined distance removed from said one light, relatively closer to the patient's mouth, whereby redundant lighting is provided at different positions inside a patient to minimize obstruction of such lighting.

4. A laryngoscope as in claim 1, further comprising a suction tube entrained along said blade means for extending into a patient's mouth and throat with such blade means, said suction tube also being adjustably supported along said handle means so that the position of a free end thereof along said blade means may be adjusted without moving said blade means.

5. A laryngoscope as in claim 1, wherein said relatively roughened side includes a plurality of miniaturized teeth means formed in said side.

6. A laryngoscope as in claim 5, wherein said teeth means are angled towards said handle means, for biasing engagement with a patient's tongue for relatively lesser blade means insertion frictional engagement, and relatively greater blade means withdrawal frictional engagement.

7. A laryngoscope as in claim 1, wherein:
    said handle means houses electric batteries therein, and is removably attached to said blade means such that the angle between said blade means and said handle means may be selectively established generally in a range of from about 45° to about 90°; and wherein said laryngoscope further includes:
    respective contacts on said blade means and said handle means for electrically interconnecting said blade means with said electric batteries;
    a pair of lights supported on said blade means, one at a relatively distal portion thereof, and the other at a relatively proximal portion thereof;
    electric wires, received in said service channels and interconnecting contacts on said blade means with said lights thereon for providing electric power to said lights from said batteries to illuminate a patient's mouth and throat; and
    a suction tube, slidably received in one of said service channels, for being selectively positioned in a patient's mouth and throat, without moving said blade means once received therein, to permit suctioning of a patient's mouth and throat.

8. A laryngoscope for use with a patient to obtain improved unobstructed viewing of a patient's tracheal process, said laryngoscope comprising:
    blade means for being inserted into the mouth of a patient for generally engaging and immobilizing the patient's tongue through contact therewith; and
    handle means, attached to said blade means, for permitting manipulation of said blade means including controlled introduction thereof into the mouth of a patient;
    wherein said blade means comprises a generally elongated member having a predetermined cross-section of compound curvature, such cross-section including a convex surface defining a primary tongue contact surface, and further including a concave surface on an opposite side of said blade means from said convex surface, said concave surface defining along said blade means a viewing channel for unobstructed viewing of the patient's tracheal process, with the patient's tongue situated on the other side of said blade means from said viewing channel, such cross-section further including a pair of gull wing members on each respective lateral edge of said convex surface, with respective junctures therewith defining service channels, and with said gull wing members being angled back towards said convex surface.

9. A laryngoscope as in claim 8, further including:
a pair of lights supported on said blade means at different axial locations and along opposing axial sides of said blade means to minimize possible obstruction of lighting therefrom; and
a suction tube slidably entrained along said blade means for adjustable positioning thereof without moving said blade means.

10. A laryngoscope as in claim 8, wherein:
said convex surface is textured for enhanced frictional engagement with a patient's tongue;
said handle means comprises a pistol-grip type handle, removably attached to said blade means, whereby the angle of attachment thereto may be varied in a range of from about 90° to about 45°;
said handle means includes batteries therein and contacts thereon; and
said blade means supports thereon lights and contacts which cooperate with said handle means contacts for powering of said lights with said batteries.

11. A laryngoscope as in claim 8, wherein said elongated blade means member is generally of constant width along the length thereof, and has a rounded distal tip.

12. A laryngoscope as in claim 8, wherein said elongated blade means member is generally tapered along the length thereof for a reducing width towards its distal tip.

13. A laryngoscope as in claim 8, wherein said service channels are formed on the convex surface side of said blade means with electric wires received in said service channels, and said gull wing members each include at least one hole formed therein for passage of light therethrough to said viewing channel side of said blade means.

14. A laryngoscope as in claim 8, wherein said service channels are formed on the viewing channel side of said blade means with electric wires received in said service channels.

15. A laryngoscope as in claim 9, wherein said suction tube is entrained along the viewing channel side of said blade means, adjacent one of said gull wing members thereof.

16. A laryngoscope, comprising:
a handle for controlled manipulation of the laryngoscope; and
an insertable, elongated blade attached to said handle for being placed in the mouth of a patient, said blade having a cross-section of compound curvature including a convex surface flanked by respective gull wing members angled back towards said convex surface defining along said blade a plurality of channel means, including an unobstructed viewing channel means for observation of a patient's tracheal process, and at least one service channel means for receiving a tube, wire conduit or the like;
wherein said blade further includes at least one relatively coarser surface on one side thereof for enhanced engagement with the patient's tongue whenever said blade is situated in a patient's mouth through manipulation thereof by a user with said handle.

17. A laryngoscope as in claim 16, further comprising:
a pair of lights respectively carried on said blade at relative distal and proximal positions thereof, and on opposing axial sides of said blade, for minimum lighting obstruction;
batteries carried in said handle;
two service channel means defined along said blade, said lights being situated adjacent respective of such service channel means;
wire conduits received in each of said service channel means; and
electric wires received in said wire conduits and interconnecting said lights with said batteries.

18. A laryngoscope as in claim 16, further comprising a suction tube slidably entrained along said blade service channel means and said handle, whereby said user may control the location of a forward tip of said tube from said handle, so as to adjust suction therewith without moving said blade or said handle.

19. A laryngoscope as in claim 16, wherein said convex surface, flanked by respective gull wing members, is opposed by a corresponding concave surface, wherein said coarser surface is formed on said convex surface, and said viewing channel means is formed by said concave surface.

20. A laryngoscope as in claim 16, wherein said handle and blade are removably attached to one another, so as to be selectively fixed with an angle therebetween in a range from about 45° to about 90°.

21. A laryngoscope for unobstructed, illuminated viewing into a patient's mouth and throat, comprising:
an elongated blade member for insertion into a patient's mouth to restrict movement of the patient's tongue and permit viewing into the patient's throat, said blade member having a compound curvature establishing a plurality of channels in relation to the patient's mouth and throat when inserted therein, said channels including an unobstructed viewing channel and three separate service channels defined by convex and concave surfaces on respective sides of said blade member and a pair of lateral gull wing members angled back towards said convex surface;
a handle, for fixed relationship attachment to said blade member, whereby a user may selectively manipulate said blade member through control of said handle, said handle also supporting electric batteries;
a coarsened surface formed on said blade member, defining a tongue contact surface thereon for enhanced engagement of a patient's tongue;
a pair of separate light means, supported on said blade member, for illuminating a patient's mouth and throat;
a pair of separate electric wire means, respectively interconnecting between said electric batteries associated with said handle and said separate light means for delivering electric power thereto, said pair of electric wire means being at least in part situated respectively in two of said service channels established by said blade member compound curvature, and
a tubular member received in the remaining service channel established with said blade member compound curvature, one end of said tubular member terminating relatively adjacent said blade member, and the other end of said tubular member extending therefrom so as to be situated outside the patient's mouth and throat while said one end and said blade member are situated therein, wherein positive or negative pressure may be applied to said tubular member other end for controlled introduction or removal, respectively, through said tubular member, of materials relative to the patient's mouth and throat.

22. A laryngoscope as in claim 21, wherein:

said blade member and handle may be adjustably fixed with an angle therebetween of from about 45° to about 90°;

said light means comprise halogen lamps;

said handle includes an adjustable finger stop member thereon; and said tubular member is adjustably received relative said blade member so that the position of said one end may be controlled without having to move said blade member or said handle.

23. A laryngoscope as in claim 22, wherein said one end of said tubular member is deflected from said blade member.

24. A laryngoscope as in claim 21, wherein said pair of light means are supported on opposing axial sides of said blade member, and one of said light means is relatively near the distal tip of said blade means and points axially therealong, while the other of said light means is relatively axially displaced from the distal tip light means and points on a path deflected from axial alignment with said blade member, whereby obstruction of said light means is minimized.

* * * * *